United States Patent [19]

Kagan

[11] 4,205,000
[45] May 27, 1980

[54] DIBENZO-OXA-BICYCLONONA-2,6-DIENES

[75] Inventor: Jacques Kagan, Wilmette, Ill.

[73] Assignee: The University of Illinois Foundation, Urbana, Ill.

[21] Appl. No.: 963,454

[22] Filed: Nov. 24, 1978

[51] Int. Cl.² .............................................. C07D 311/02
[52] U.S. Cl. .......................... 260/345.2; 260/570.8 TC; 260/570.9
[58] Field of Search ..................................... 260/345.2

[56] References Cited
U.S. PATENT DOCUMENTS 3,472,869  10/1969  Humber et al. .................... 260/326.5

FOREIGN PATENT DOCUMENTS 1377411  11/1964  France ............................ 260/570.8 TC

*Primary Examiner*—Nicky Chan
*Attorney, Agent, or Firm*—Mathew L. Kalinowski

[57] ABSTRACT

The compound 1,2,5,6-dibenzo-9-oxa-[3.3.1]-bicyclonona-2,6-diene is prepared by the condensation of two moles of phenylacetaldehyde in the presence of a strong acid such as fluorosulfuric acid. The compound is a useful intermediate in the synthesis of pharmaceuticals, for example, antispasmodic and antiinflammatory agents.

10 Claims, No Drawings

DIBENZO-OXA-BICYCLONONA-2,6-DIENES

This invention relates to dibenzo-oxa-bicyclonona-2,6-dienes and their preparation. In a particular aspect, this invention relates to 1,2,5,6-dibenzo-9-oxa-[3.3.1]-bicyclonona-2,6-diene and its preparation.

The patent compound, oxa-9-cyclonona-2,6-diene (1), is known, and its preparation is disclosed by Stetter, et al., Chem. Ber., 101, 2889 (1968). The preparation starts with cyclo-octadiene and includes the steps of mercuration, treatment with KI, iodination, and finally treatment with alcoholic KOH to obtain the desired product. The preparation of (2), the dibenzo analog, however, cannot be successfully accomplished by this method or by any other method reported for the preparation of the ring system represented by (1).

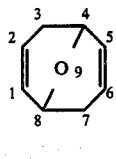
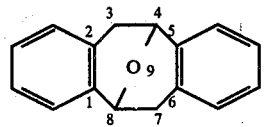

In accordance with this invention, a facile, single step process has been developed for the preparation of dibenzo-oxa-bicyclonona-2,6-dienes. The process involves the condensation of two molecules of phenylacetaldehyde, or substituted phenylacetaldehyde, in the presence of a strong acid. Phenylacetaldehydes capable of undergoing this condensation can be represented by the formula

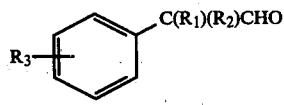

where $R_1$ and $R_2$ can be hydrogen, alkyl, phenyl, or carboalkoxy groups, and $R_3$ can be hydrogen or an alkyl group. Preferred phenylacetaldehydes are selected from the group consisting of $C_6H_5CH_2CHO$, $C_6H_5CH(CH_3)CHO$, $C_6H_6CH(C_6H_5)CHO$, and $C_6H_5C(CH_3)(CO_2C_2H_5)CHO$.

The strong acid required for the condensation step of this invention can be characterized as a strong proton donor or a Bronsted acid. Satisfactory condensation results are obtained with acids varying in strength from sulfuric acid to fluorosulfuric acid. In addition to these two acids, such acids as perchloric acid, chlorosulfonic acid, alkane sulfonic acids, and p-toluene sulfonic acid can be used.

The condensation is effected by stirring with cooling the phenylacetaldehyde compound with the strong acid under anhydrous conditions. An inert solvent such as $CCl_4$ can be used. The condensation product is isolated by pouring the reaction mixture over ice and by extraction with $CCl_4$ and/or ether. The extract is washed with $NaHCO_3$, dried, and concentrated under vacuum to yield a residue comprising the desired dibenzo-oxa-bicyclonona-2,6-diene. The product can be further purified, if necessary, by thin layer chromatography.

The dibenzo-oxa-bicyclonona-2,6-dienes of this invention are useful intermediates for the preparation of valuable pharmaceuticals. For example, (2) can be readily converted to the ketone (3) by the following reaction scheme

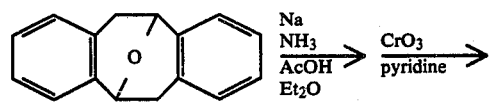

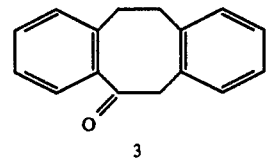

In a first step, (2) in acetic acid-ether solution is reduced to the alcohol by treatment with sodium is liquid ammonia at $-78°$ C. In a second step, the alcohol is oxidized in pyridine solution with chromic oxide.

The ketone (3) can be converted as disclosed in French Pat. No. 1,377,411 by treatment with a Grignard reagent prepared from magnesium and a dialkylaminoalkylhalide to yield the product (4) which is an effective antispasmodic agent:

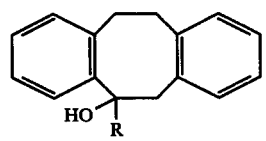

where R is $(CH_3)_2N(CH_2)_3-$.

The ketone (3) can also be converted as disclosed in U.S. Pat. No. 3,472,869 by treatment with $C_6H_5CH_2N(CH_3)_2$ to yield the product (5) which is an effective antiinflammatory agent:

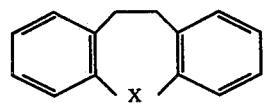

where X is $C(OH)RCH_2$ and R is $o-(CH_3)_2NCH_2C_6H_5$.

The above-cited patents are incorporated herein by reference to illustrate the utility of the compounds of this invention.

PREFERRED EMBODIMENTS OF THE INVENTION

The invention can be more readily understood and illustrated by reference to the following procedures and working examples.

EXAMPLE 1

Condensation of phenylacetaldehyde

An ice-cold mixture of 2 g of phenylacetaldehyde in 20 ml of $CCl_4$ and 8 ml of $FSO_3H$ was stirred for 45 min at $0°$ C., poured over ice, and extracted successively with 550 ml of $CCl_4$ and 300 ml of ether. The extracts were washed with dilute $NaHCO_3$, combined and dried over $MgSO_4$, and concentrated under vacuum to yield 1.09 g of residue, which NMR indicated to be a single product. After recrystallization from $CCl_4$-isopropyl ether, the product melted at $140°-141°$ C.

This product resulted from the condensation of two molecules of phenylacetaldehyde since mass spectrometry indicated a molecular weight of 222. Infrared as well as C-13 NMR spectra showed no carbonyl group. The IR spectrum showed a strong C-O band at 1070 cm$^{-1}$, and the C-13 NMR in CDCl$_3$ displayed two aliphatic carbons at 36.1 and 69.5, and six aromatic signals at 125.1, 125.9, 126.8, 129.1, 131.6, and 137.7 ppm. This small number of signals demanded that the molecule be quite symmetrical, a fact also apparent from the proton NMR spectrum, which showed aromatic signals at 6.7–7.1, in addition to only one methine at 5.13 and two methylene protons at 3.45 and 2.63 ppm, with a geminal coupling constant of 16 Hz, and vicinal constants of 0 and 6 Hz. The structure of the product was unequivocally established by single crystal X-ray crystallographic analysis, and shown to be that shown in (2), namely 1,2,5,6-dibenzo-9-oxa-[3.3.1]-bicyclonona-2,6-diene.

EXAMPLE 2

Condensation of diphenylacetaldehyde

A solution of 100 mg of (C$_6$H$_5$)$_2$CHCHO in 0.3 ml of CCl$_4$ was added to 0.5 ml of FSO$_3$H at $-78°$ C. The magnetically stirred mixture was allowed to return to room temperature in 90 min, was poured over ice, and was then extracted successively with 40 ml of CCl$_4$ ml of ether. The organic extracts were washed with 5% aqueous NaHCO$_3$, combined, dried over MgSO$_4$, and concentrated, yielding 50 mg of product. The product is 1,2,5,6-dibenzo-9-oxa-3,7-diphenyl-[3.3.1]-bicyclonona-2,6-diene.

EXAMPLE 3

Condensation of phenyl carboethoxypropionaldehyde

A mixture of 206 mg of C$_6$H$_5$C(CH$_3$)(CO$_2$C$_2$H$_5$)-CHO and 0.45 ml of FSO$_3$H was allowed to stand at 0° C. for 1 hr, and was then poured onto ice. After successive extractions with 30 ml of CCl$_4$ and 30 ml of ether, the organic extracts were washed with 5% aqueous NaHCO$_3$, combined, dried over MgSO$_4$, and concentrated under vacuum, yielding about 200 mg of an oil. Preparative thin layer chromatography over silica gel using hexane-ethyl acetate (3:1) yielded as the principal product 1,2,5,6-dibenzo-9-oxa-3,7-dimethyl-3,7-dicarboethoxy-[3.3.1]-bicyclonona-2,6-diene.

EXAMPLE 4

Condensation of methylphenylacetaldehyde

The aldehyde C$_6$H$_5$CH(CH$_3$)CHO was condensed with fluorosulfuric acid according to the procedure of Example 1. The principal product was 1,2,5,6-dibenzo-9-oxa-3,7-dimethyl-[3.3.1]-bicyclonona-2,6-diene.

Although this invention has been described in detail with particular reference to certain preferred embodiments thereof, it is understood that variations and modifications can be effeted within the scope of the appended claims. It is intended that all matter contained in the above description and equations shall be interpreted in an illustrative and not in a limiting sense.

What is claimed is:

1. The compound

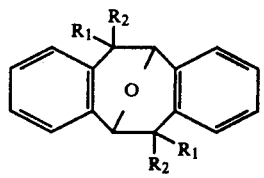

where R$_1$ and R$_2$ are selected from the group consisting of hydrogen, methyl, phenyl, and carboethoxy.

2. The compound of claim 1 wherein R$_1$ and R$_2$ are hydrogen.

3. The compound of claim 1 wherein R$_1$ is phenyl and R$_2$ is hydrogen.

4. The compound of claim 1 wherein R$_1$ is methyl and R$_2$ is carboethoxy.

5. The compound of claim 1 wherein R$_1$ is methyl and r$_2$ is hydrogen.

6. A process for preparing dibenzo-9-oxa-bicyclonona-2,6-dienes comprising condensing in the presence of a strong acid a phenylacetaldehyde having the formula

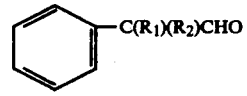

where R$_1$ and R$_2$ are selected from the group consisting of hydrogen, methyl, phenyl, and carboethoxy, said strong acid having an acid strength within the range defined by sulfuric acid and fluorosulfuric acid.

7. The process of claim 6 wherein R$_1$ and R$_2$ are hydrogen and the strong acid is fluorosulfuric acid.

8. The process of claim 6 wherein R$_1$ is phenyl, R$_2$ is hydrogen, and the strong acid is fluorosulfuric acid.

9. The process of claim 6 wherein R$_1$ is methyl and R$_2$ is carboethoxy, and the strong acid is fluorosulfuric acid.

10. The process of claim 6 wherein R$_1$ is methyl, R$_2$ is hydrogen, and the strong acid is fluorosulfuric acid.